United States Patent
Blom

(10) Patent No.: US 10,398,419 B2
(45) Date of Patent: *Sep. 3, 2019

(54) SELF-ADJUSTING MEDICAL DEVICE

(71) Applicant: Hansa Medical Products, Inc., Carmel, IN (US)

(72) Inventor: Eric D. Blom, Carmel, IN (US)

(73) Assignee: Hansa Medical Products, Inc., Carmel, IN (US)

(*) Notice: Subject to any disclaimer, the term of this patent is extended or adjusted under 35 U.S.C. 154(b) by 158 days.

This patent is subject to a terminal disclaimer.

(21) Appl. No.: 15/286,136

(22) Filed: Oct. 5, 2016

(65) Prior Publication Data

US 2017/0020498 A1     Jan. 26, 2017

Related U.S. Application Data

(63) Continuation of application No. 13/318,581, filed as application No. PCT/US2010/031579 on Apr. 19, (Continued)

(51) Int. Cl.
| | | |
|---|---|---|
| *A61B 17/24* | (2006.01) | |
| *A61F 2/20* | (2006.01) | |
| *A61B 17/00* | (2006.01) | |

(52) U.S. Cl.
CPC .......... *A61B 17/0057* (2013.01); *A61B 17/24* (2013.01); *A61F 2/203* (2013.01); (Continued)

(58) Field of Classification Search
CPC ............... A61B 17/0057; A61B 17/24; A61B 2017/00592; A61B 2017/00606; (Continued)

(56) References Cited

U.S. PATENT DOCUMENTS 4,402,314 A   9/1983   Goode
4,435,853 A   3/1984   Blom et al.
(Continued)

FOREIGN PATENT DOCUMENTS

| GB | 2409978 A | 7/2005 |
| JP | 2009061187 A | 3/2009 |
| WO | 1997/027898 A1 | 8/1997 |

OTHER PUBLICATIONS

Patent Examination Report No. 1 from AU 2010245115, dated Jun. 3, 2013 (4 pages).
(Continued)

*Primary Examiner* — Jocelin C Tanner
(74) *Attorney, Agent, or Firm* — Daniel J. Sepanik, Esq.; Harness, Dickey & Pierce, P.L.C.

(57) ABSTRACT

A device for sealing a fistula includes a first flange for orienting against a first wall of the fistula, a second flange for orienting against a second wall of the fistula, and at least one stem coupling the first and second flanges. Illustratively, the at least one stem is elastomeric. The stem(s) exhibit(s) an elongation of greater than about 0.6 mm/N of force applied between the first and second flanges in the range of elongation of about 0 mm to about 15 mm. Additionally or alternatively illustratively, the stem(s) comprise(s) (an) elastomeric tube(s) including (a) wall section(s) having a varying radius along its (their) length(s). Additionally or alternatively illustratively, the stem(s) pass(es) through (respective) opening(s) provided in at least one of the first and second flanges to permit adjustment of the location of at least one of the first and second flanges along the length of the stem(s).

19 Claims, 5 Drawing Sheets

Related U.S. Application Data 2010, now Pat. No. 9,801,617, which is a continuation of application No. 12/436,230, filed on May 6, 2009, now abandoned.

(52) U.S. Cl.
CPC .............. *A61B 2017/00592* (2013.01); *A61B 2017/00606* (2013.01); *A61B 2017/00619* (2013.01); *A61B 2017/00641* (2013.01); *A61B 2017/00862* (2013.01)

(58) Field of Classification Search
CPC ........... A61B 2017/00619; A61B 2017/00641; A61B 2017/00862; A61F 2/203
See application file for complete search history.

(56) References Cited

U.S. PATENT DOCUMENTS

| | | |
|---|---|---|
| 4,596,579 A | 6/1986 | Pruitt |
| 4,614,516 A | 9/1986 | Blom et al. |
| 4,820,304 A | 4/1989 | Depel et al. |
| 4,902,508 A | 2/1990 | Badylak et al. |
| 4,911,716 A | 3/1990 | Blom et al. |
| 4,956,178 A | 9/1990 | Badylak et al. |
| 5,064,433 A | 11/1991 | Blom et al. |
| 5,300,119 A | 4/1994 | Blom |
| 5,350,399 A | 9/1994 | Erlebacher et al. |
| 5,352,463 A | 10/1994 | Badylak et al. |
| 5,352,821 A | 10/1994 | Goda et al. |
| 5,372,821 A | 12/1994 | Badylak et al. |
| 5,445,833 A | 8/1995 | Badylak et al. |
| 5,507,809 A | 4/1996 | Blom |
| 5,516,533 A | 5/1996 | Badylak et al. |
| 5,554,389 A | 9/1996 | Badylak et al. |
| 5,571,180 A | 11/1996 | Blom |
| 5,573,784 A | 11/1996 | Badylak et al. |
| 5,641,518 A | 6/1997 | Badylak et al. |
| 5,645,860 A | 7/1997 | Knapp, Jr. et al. |
| 5,711,696 A | 1/1998 | Maeda et al. |
| 5,753,267 A | 5/1998 | Badylak et al. |
| 5,755,791 A | 5/1998 | Whitson et al. |
| 5,762,966 A | 6/1998 | Knapp, Jr. et al. |
| 5,788,625 A | 8/1998 | Plouhar et al. |
| 5,861,003 A | 1/1999 | Latson et al. |
| 5,866,414 A | 2/1999 | Badylak et al. |
| 5,885,619 A | 3/1999 | Patel et al. |
| 5,919,231 A | 7/1999 | Blom et al. |
| 5,922,028 A | 7/1999 | Plouhar et al. |
| 5,941,898 A | 8/1999 | Moenning et al. |
| 5,955,110 A | 9/1999 | Patel et al. |
| 5,968,075 A | 10/1999 | Wood |
| 5,968,096 A | 10/1999 | Whitson et al. |
| 5,997,575 A | 12/1999 | Whitson et al. |
| 6,096,347 A | 8/2000 | Geddes et al. |
| 6,099,567 A | 8/2000 | Badylak et al. |
| 6,176,880 B1 | 1/2001 | Plouhar et al. |
| 6,187,039 B1 | 2/2001 | Hiles et al. |
| 6,206,931 B1 | 3/2001 | Cook et al. |
| 6,251,143 B1 | 6/2001 | Schwartz et al. |
| 6,264,992 B1 | 7/2001 | Voytik-Harbin et al. |
| 6,312,474 B1 | 11/2001 | Francis et al. |
| 6,331,319 B1 | 12/2001 | Badylak et al. |
| 6,358,284 B1 | 3/2002 | Fearnot et al. |
| 6,375,989 B1 | 4/2002 | Badylak et al. |
| 6,444,229 B2 | 9/2002 | Voytik-Harbin et al. |
| 6,468,314 B2 | 10/2002 | Schwartz et al. |
| 6,485,723 B1 | 11/2002 | Badylak et al. |
| 6,508,784 B1 | 1/2003 | Shu |
| 6,545,042 B2 | 4/2003 | Sung et al. |
| 6,616,675 B1 | 9/2003 | Evard et al. |
| 6,624,138 B1 | 9/2003 | Sung et al. |
| 6,638,312 B2 | 10/2003 | Plouhar et al. |
| 6,652,594 B2 | 11/2003 | Francis et al. |
| 6,776,797 B1 | 8/2004 | Blom et al. |
| 6,849,273 B2 | 2/2005 | Spievack |
| 6,852,339 B2 | 2/2005 | Spievack |
| 6,861,074 B2 | 3/2005 | Spievack |
| 6,869,619 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,998,418 B1 | 2/2006 | Sung et al. |
| 7,175,841 B2 | 2/2007 | Badylak et al. |
| RE39,923 E | 11/2007 | Blom |
| 7,306,627 B2 | 12/2007 | Tanagho et al. |
| 7,361,195 B2 | 4/2008 | Schwartz et al. |
| 7,520,897 B2 | 4/2009 | Seder et al. |
| 7,931,671 B2 | 4/2011 | Tenerz |
| 9,801,617 B2 * | 10/2017 | Blom ................. A61B 17/0057 |
| 2003/0060786 A1 | 3/2003 | Olsen et al. |
| 2003/0100920 A1 | 5/2003 | Akin et al. |
| 2006/0157061 A1 | 7/2006 | Loyd et al. |
| 2006/0206146 A1 | 9/2006 | Tenerz |
| 2008/0071310 A1 | 3/2008 | Hoffman et al. |
| 2009/0054979 A1 | 2/2009 | Debry et al. |
| 2010/0042144 A1 | 2/2010 | Bennett |
| 2012/0266891 A1 | 10/2012 | Resca et al. |

OTHER PUBLICATIONS

Patent Examination Report No. 2 from AU 2010245115, dated Sep. 11, 2013 (3 pages).
Patent Examination Report No. 3 from AU 2010245115, dated May 29, 2014 (4 pages).
International Search Report/Written Opinion for PCT International Application No. PCT/US2010/031579, dated Jul. 8, 2010.
Blom, "Gestione Clinica Delle Complicanze da intervento di Ripristino Vocale Dopo Fistola Tracheo-Esofagea," Sep. 23, 1998, XXII Convegno Nazionale Di Aggiornamento A. O. O. I. Impianti Fonatori Nel Laringectomizzato (pp. 127-141).
Hilgers, et al, "A Thin Tracheal Silicone Washer to Solve Periprosthetic Leakage in Laryngectomies: Direct Results and Long-Term Clinical Effects," Apr. 2008, The Laryngoscope, vol. 118 (pp. 640-645).
European Search Report and Written Opinion for EP10772449.4, dated Jul. 13, 2013.
Schmitz et al, "A simple technique for closure of persistent tracheoesophageal fistula after total laryngectomy," Otoloaryngology—Head and Neck Surgery (2009) pp. 140, 601-603.
Bonelli et al, "Parlane Senza Laringe," Edizioni Omega, 1984 (8 pages).
Medtronic ENT Product & Instrument Catalog, 2005 (3 pages).
SiiMed Septal Button brochure, date unknown (2 pages).
Price et al, "Computed Tomography for Constructing Custom Nasal Septal Buttons," Arch. Otolaryngol Head Neck SurgNol. 129, Nov. 2003 (pp. 1236-1239).
Manning M. Goldsmith, "The adjustable two-piece nasal septal button," Otolaryngology—Head and Neck Surgery, Jul. 25, 1988 (2 pages).
Hood Nasal Septal Button brochure, 1992 (2 pages).
Eliachar et al, "Improved nasal septal prosethic button," Otolamygology—Head and Neck Surgery, Jul. 29, 1994 (pp. 347-349).
Xomed-Treace Catalog, Head and Neck Products, date unknown (pp. 129, 131, 133).
Medtronic Septal Button product pamphlet and photographs, Dec. 2006 (6 pages).

\* cited by examiner

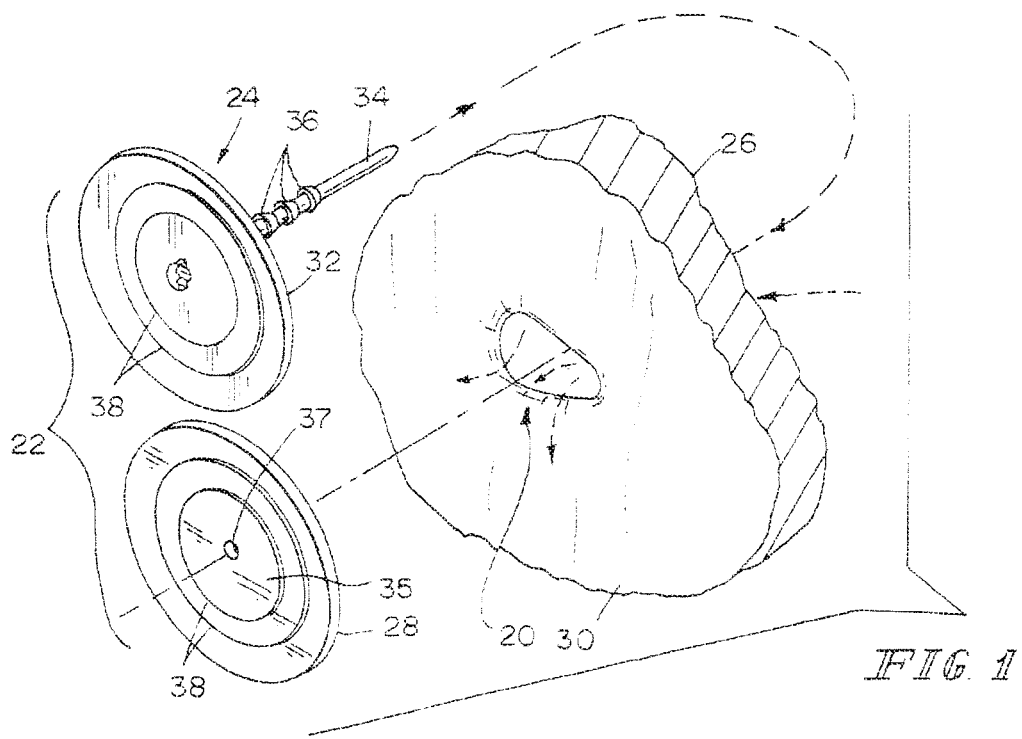
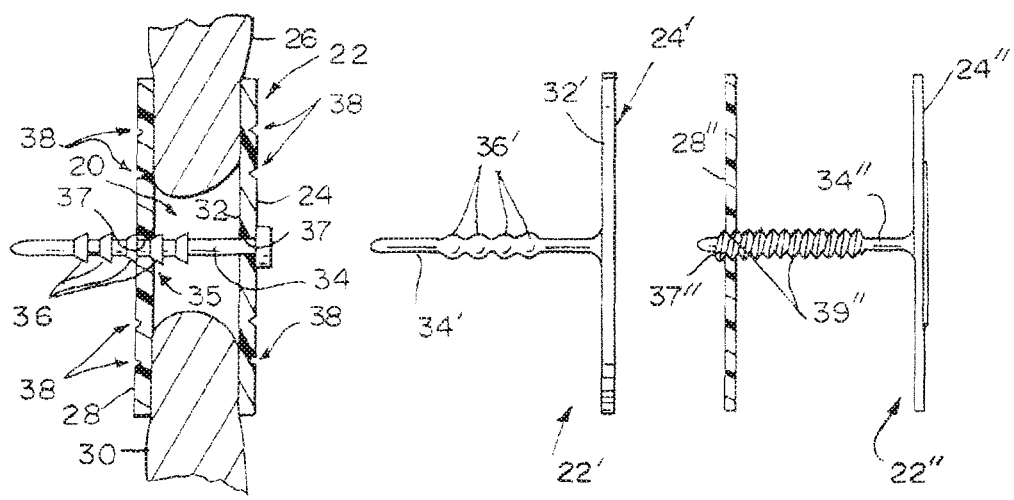

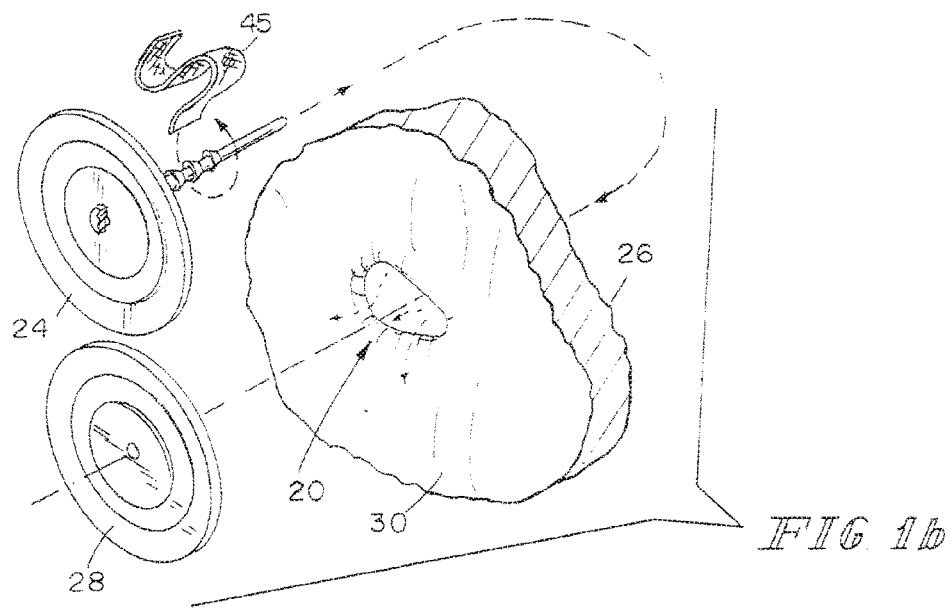
FIG 1b
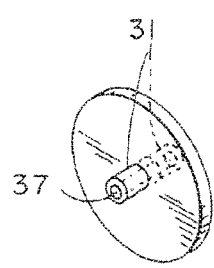
FIG 1a
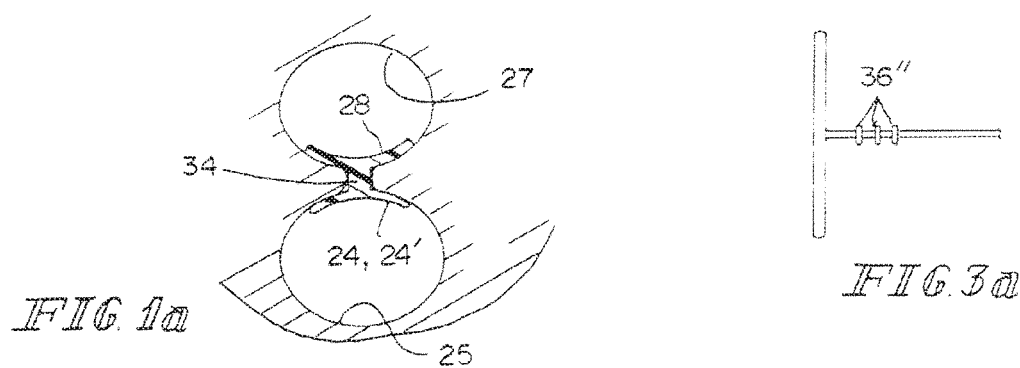
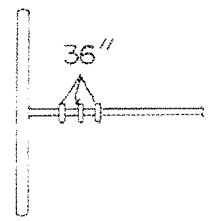
FIG 3a
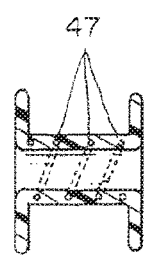
FIG 2a
FIG 8a

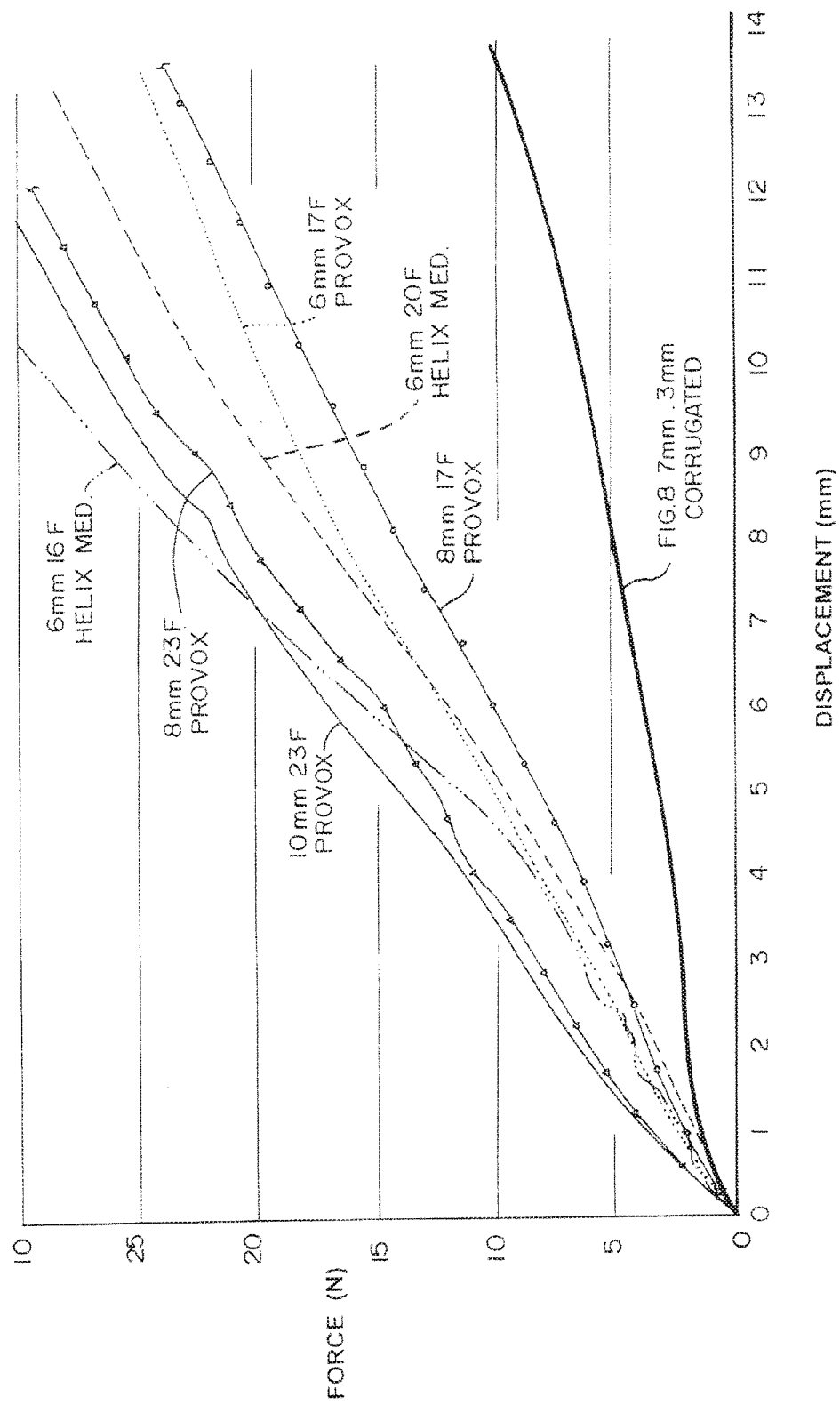

SELF-ADJUSTING MEDICAL DEVICE

CROSS-REFERENCE TO RELATED APPLICATIONS

This application is a continuation of U.S. application Ser. No. 13/318,581, filed Nov. 2, 2011 (now U.S. Pat. No. 9,801,917), which is a National Phase of PCT/US2010/031579, filed Apr. 19, 2010 (now WO 2010/129162A1), which is a continuation of U.S. application Ser. No. 12/436,230, filed May 6, 2009 (now abandoned). The entire disclosures of each of the above applications are incorporated herein by reference.

FIELD

The present disclosure relates to a device for sealing a fistula.

BACKGROUND

This section provides background information related to the present disclosure which is not necessarily prior art.

Devices for sealing a fistula in a patient's tissue are illustrated and described in: Blom, Eric D., "Gestione clinica delle complicanze da intervento di ripristino vocale dopo fistola tracheo-esofagea," XXII Convegno Nazionale Di Aggiornamento A. O. O. I. Impianti Fonatori Nel Laringectomizzato, Rome, Sep. 23, 1998, pp. 127-141; and, Hilgers, Frans J. M., Jessica Soolsma, Annemieke H. Ackerstaff, Fons J. M. Balm, I. Bing Tan and Michiel W. M. van den Brekel, "A Thin Tracheal Silicone Washer to Solve Periprosthetic Leakage in Laryngectomies: Direct Results and Long-Term Clinical Effects," The Laryngoscope, vol. 118, pp. 640-645, April 2008. The disclosures of these references are hereby incorporated herein by reference. This listing is not intended as a representation that a complete search of all relevant prior art has been conducted, or that no better references than those listed exist. Nor should any such representation be inferred.

There are also the devices and methods illustrated and described in U.S. Pat. Nos. 4,911,716; 5,919,231; and, 6,776,797. The disclosures of these references are hereby incorporated herein by reference. This listing is not intended as a representation that a complete search of all relevant prior art has been conducted, or that no better references than those listed exist. Nor should any such representation be inferred.

SUMMARY

This section provides a general summary of the disclosure, and is not a comprehensive disclosure of its full scope or all of its features.

According to an aspect of the disclosure, a self-adjusting device for sealing a fistula includes a first flange for orienting against a first wall of the fistula, a second flange for orienting against a second wall of the fistula, and at least one stem for coupling the first and second flanges. The stem or stems exhibit an elongation of greater than about 0.6 mm/N of force applied between the first and second flanges in the range of elongation between about 0 mm to about 15 mm.

According to another aspect of the invention, a self-adjusting device for sealing a fistula includes a first flange for orienting against a first wall of the fistula, a second flange for orienting against a second wall of the fistula, and an elastomeric stem for coupling the first and second flanges. The stem comprises a tube including a wall section having a varying radius along its length.

According to another aspect, a self-adjusting device for sealing a fistula includes a first flange for orienting against a first wall of the fistula, a second flange for orienting against a second wall of the fistula, and at least one elastomeric stem for coupling the first and second flanges to maintain them in sealing orientation against the first and second walls, respectively, of the fistula.

According to another aspect, an adjustable device for sealing a fistula includes a first flange for orienting against a first wall of the fistula, a second flange for orienting against a second wall of the fistula, and at least one stem coupling the first and second flanges. The at least one stem passes through a respective at least one opening provided in at least one of the first and second flanges to permit adjustment of the location of said at least one of the first and second flanges along the length of the at least one stem.

Illustratively according to various aspects, the stem comprises a hollow tubular portion.

Further illustratively according to various aspects, the stem comprises a corrugated wall section.

Illustratively according to various aspects, at least one of the first and second flanges and the stem are formed integrally. Illustratively according to various aspects, the first flange, the second flange and the stem are all integral. Alternatively illustratively according to various aspects, the stem is not integral with, but rather, is attached to at least one of the first and second flanges.

Illustratively according to various aspects, at least one of the first and second flanges comprises an elastomeric first and/or second flange.

Illustratively according to various aspects, an opening is provided through at least one of the first and second flanges and the stem is inserted into the opening until the said at least one of the first and second flanges reaches the desired location along the length of stem.

Additionally illustratively according to various aspects, the stem is provided with enlargements at intervals along its length. Illustratively, the enlargements comprise somewhat spherical-, disk-, cone- or arrowhead-shaped enlargements. Further illustratively, the enlargements are substantially uniformly spaced along at least a portion of the length of stem.

Illustratively according to various aspects, the first and second flanges are generally circular in plan view.

Illustratively according to various aspects, at least one of the first and second flanges includes at least one guide to guide trimming of said at least one of the first and second flanges from a manufactured size to suit the needs of a particular application.

Illustratively according to various aspects, at least one of the first and second flanges comprises a portion curved to approximate the curvature of a wall of the tissue through which the fistula extends.

Illustratively according to various aspects, the stem includes a spring.

Further illustratively according to various aspects, the device includes a tissue graft material to promote healing of the fistula.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 illustrates a fragmentary perspective view of a fistula and a device for sealing the fistula being placed in the fistula;

FIG. 1a illustrates a horizontal sectional view looking downward through the neck, trachea and esophagus of a wearer;

FIG. 1b illustrates an optional detail of the device illustrated in FIG. 1;

FIG. 2 illustrates a fragmentary partial longitudinal sectional view of the fistula and device illustrated in FIG. 1 with the device in place sealing the fistula;

FIG. 2a illustrates an optional detail of the device illustrated in FIGS. 1-2;

FIG. 3 illustrates an elevational view of another configuration of a component of the device illustrated in FIGS. 1 and 2;

FIG. 3a illustrates an optional detail of the devices illustrated in FIGS. 1-3;

FIG. 4 illustrates an elevational view of another configuration of the devices illustrated in FIGS. 1-3;

FIG. 8a illustrates an optional detail of the device illustrated in FIGS. 5, 6 and 8;

FIG. 10 illustrates enlarged views of portions of the graphs illustrated in FIG. 9.

Corresponding reference numerals indicate corresponding parts throughout the several views of the drawings.

DETAILED DESCRIPTION

Figures 5, 6:
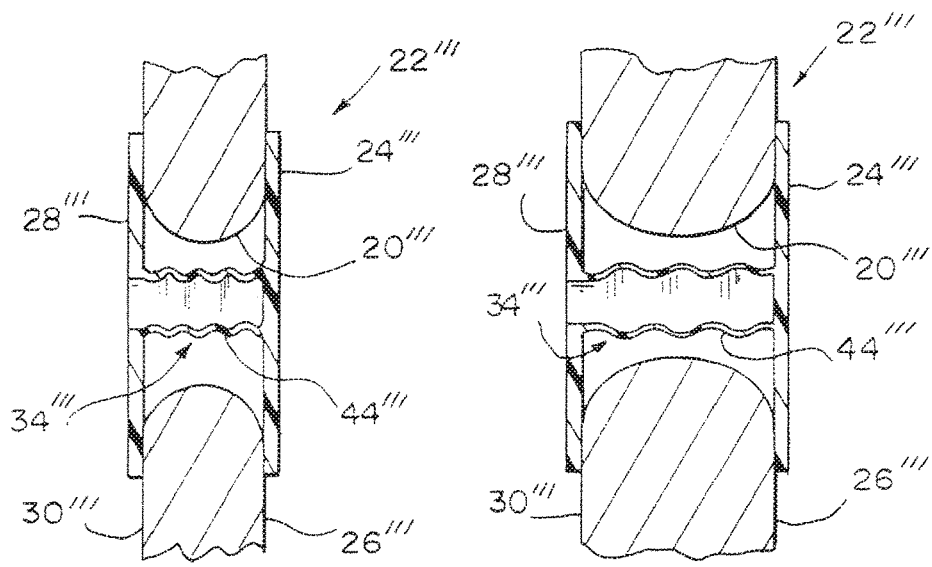
FIG. 5 illustrates a fragmentary partial longitudinal sectional view of another fistula and device in place sealing the fistula.
FIG. 6 illustrates a fragmentary partial longitudinal sectional view of the device illustrated in FIG. 5, with the tissue through which the fistula passes swollen.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

A difficulty associated with sealing a fistula in a patient's tissue is that the spacing between the opposite walls of the tissue through which the fistula extends tends to fluctuate. For example, swelling of the tissue results in an increase in its thickness. Receding of the tissue results in a decrease in its thickness. If a flanged device including two flanges joined by a stem which passes through the fistula is used to close the fistula, swelling of the tissue can cause the patient discomfort, can cause further swelling and resultant overgrowth of tissue around the flange(s), and can cause tissue damage. It places some additional stress on the stem, but the flanges are retained tightly against their respective opposite walls of the tissue. The fistula remains sealed by the device, which thus continues to serve its fistula-sealing purpose.

The latter event, thinning of the tissue between the opposite walls, causes the opposite walls of the tissue to recede, pulling away from their respective flanges. If this happens, then fluids (gases and/or liquids) can pass between one of the opposite walls and its respective flange, through the fistula, and between the other of the opposite walls and its respective flange on the other side. The passage of fluid from one side of the fistula to the other, among other things, may adversely impact the ability of the tissue to heal and the fistula to close. Additionally, depending upon the location of the fistula, further difficulty may attend such fluid leakage. For example, if the fistula is a tracheoesophageal fistula, fluids from the esophagus leaking into the trachea and lungs can have severe adverse consequences. The individual experiencing such difficulty may have to be fed through a feeding tube. These difficulties may result in extended hospital stays with their attendant economic, and other, consequences. For fistulas in other locations, bodily fluids leaking externally can soil the patient's clothing, resulting in annoyance and embarrassment. Air leakage can also be annoying and embarrassing.

Referring now to FIGS. 1-3, a self-adjusting biflanged pharyngocutaneous fistula 20-sealing device 22 or 22' includes an illustratively elastomeric flange 24 or 24' for orienting against the pharyngeal wall 26 of the tissue through which fistula 20 has developed, and an illustratively elastomeric flange 28 for orienting against the cutaneous wall 30 of the tissue. One of the flanges 24 or 24', 28, illustratively, flange 24 or 24', has protruding from a surface 32 or 32' thereof an elastomeric stem 34 or 34' provided with illustratively somewhat spherical-, disk-(see FIG. 3a, 36"), cone- or arrowhead- or otherwise-shaped enlargements 36, 36', 36" at intervals, illustratively regular intervals, along at least a port of its length. The stem 34 or 34' can be solid or hollow tubular in cross-section transverse to its longitudinal extent. Enlargements 36, 36', 36" may be uniformly spaced or non-uniformly spaced along stem 34 or 34' according to the needs of a particular application. The flange 24' and stem 34' can be formed integrally, or stem 34 can be glued, heat bonded or otherwise attached to flange 24. For example, an opening 37 can be provided through flange 24 and stem 34 snapped and slid through the opening 37 until flange 24 reaches the desired location along the length of stem 34. Alternatively, the opening 37 and stem 34 may be sized so that the opening 37 holds the stem 34 frictionally. The opening 37 may be provided with (an) axially extending sleeve(s) 31 of short length (see FIG. 2a) extending in one or the other or both axial directions of the opening 37 to aid in frictionally holding the stem 34.

While the flanges 24, 28 are both illustrated as flat circular, somewhat coin- or disk-shaped, both need not be the same shape, and neither need be circular or flat. The sizes (diameters in the illustrated embodiment, thicknesses and curvatures) of flanges 24 or 24', 28 may be determined by the use(s) for which the device 22 or 22' is intended. For example, and with reference to FIG. 1a, if a device 22 or 22' is to be used to close a tracheoesophageal fistula, the clinician might want both flanges 24 or 24', 28 to be concavely curved to match the curvatures of the walls of the trachea 25 and of the esophagus 27. Illustrative characteristics of the flanges 24 or 24', 28 and stem 34 or 34' are that they may be made of "glass clear" silicone (so that the underlying tissue may be readily observed without having to remove the device 22 or 22') having a durometer of, for example, 50. Suitable thicknesses for flanges 24 or 24', 28 might be 0.020 inch, 0.030 inch and 0.040 inch. The flanges 24 or 24', 28 can be manufactured with uniform thicknesses, or provided with, for example, thicker central regions to reduce flexing when they are in use. See FIG. 4, flange 24". Additionally, the flange 28 may be provided with a somewhat more rigid, less elastomeric, region 35 (see FIG. 1) around its central opening 37, for example, provided by way of an insert during molding or other manufacture of the device, to further reduce the likelihood that the flange 28 would slip backward off the stem 34, 34' in use, for example, when the tissue between flanges 24, 24' and 28 swells. The illustrated flanges 24, 28 may be provided with concentric grooves or separating lines 38 facilitating cutting them down from their manufactured sizes to smaller sizes to suit the needs of a particular application.

In another device 22" illustrated in FIG. 4, the elastomeric stem 34" and opening 37" can be provided with complementary threads 39" permitting the flange 28" to be threaded onto the stem 34" and drawn initially into sealing contact with the wall 30.

Figures 7, 8:
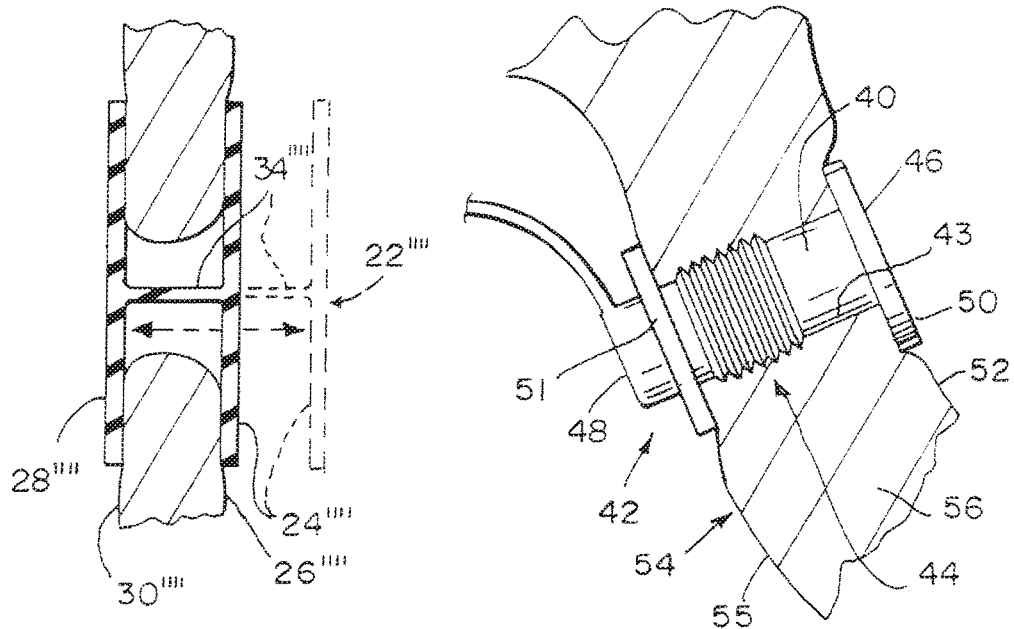
FIG. 7 illustrates a fragmentary partial longitudinal sectional view of another fistula and a device in place sealing the fistula.
FIG. 8 illustrates a fragmentary partial longitudinal sectional view of another fistula and a device in place sealing the fistula.

In another device 22''' illustrated in FIGS. 5-6, the elastomeric stem 34''' is formed as a hollow tube with a corrugated (corrugated meaning of varying radius as the observer moves along its axial length and includes pleated sections, wavelike sections, accordion sections and so on, creating alternating furrows and ridges or crests and troughs, as in the embodiments illustrated in FIGS. 5, 6 and 8) section 44''' which, in its manufactured, unstressed configuration provides the least distance between flanges 24''', 28'''. Section 44''' may also be characterized by having a thinner wall thickness than the non-corrugated regions of stem 34'''. Generally, a length may be chosen that is intermediate between the anticipated minimum and maximum thicknesses that the device 22''' will need to span. Thus, as the tissue thickens (compare FIGS. 5 and 6), owing to various phenomena, the section 44''' stretches to accommodate the attendant increase in the length stem 34''' must span owing to the engagement of flanges 24''', 28''' with their respective walls 26''', 30'''. Similarly, if the tissue thickness decreases, section 44''' automatically accommodates this shrinkage.

In yet another device 22'''' illustrated in FIG. 7, the elastomeric stem 34'''' may be somewhat the configuration of a rubber band and be fixed at its ends to both of flanges 24'''', 28''''. The tension of the stem 34'''' maintains the flanges 24'''', 28'''' in fluid sealing contact with their respective surfaces 26'''', 30''''.

Devices 22, 22', 22", 22''', 22'''' of this type may be used to seal fistulas in various regions of the body, such as the previously mentioned pharyngocutaneous fistulas, oro-nasal fistulas, septal fistulas, oro-cutaneous fistulas, tracheocutaneous fistulas, rectal-vaginal fistulas, and so on, and may facilitate eventual healing. With reference to FIG. 1b, in many of these devices, healing may also be promoted by incorporation with or into the devices 22, 22', 22", 22''', 22'''' of tissue graft material 45 of the general types illustrated in any of U.S. Pat. Nos. 4,902,508; 4,956,178; 5,352,463; 5,372,821; 5,445,833; 5,516,533; 5,554,389; 5,573,784; 5,641,518; 5,645,860; 5,711,969; 5,753,267; 5,755,791; 5,762,966; 5,788,625; 5,866,414; 5,885,619; 5,922,028; 5,955,110; 5,968,096; 5,997,575; 6,096,347; 6,099,567; 6,176,880; 6,187,039; 6,206,931; 6,251,143; 6,264,992; 6,312,474; 6,331,319; 6,358,284; 6,375,989; 6,444,229; 6,468,314; 6,485,723; 6,545,042; 6,624,138; 6,638,312; 6,652,594; 6,849,273; 6,852,339; 6,861,074; 6,869,619; 6,887,495; 6,890,562; 6,890,563; 6,890,564; 6,893,666;

6,998,418; 7,175,841; 7,306,627; and, 7,361,195. Again, the disclosures of these references are hereby incorporated herein by reference. This listing is not intended as a representation that a complete search of all relevant prior art has been conducted, or that no better references than those listed exist. Nor should any such representation be inferred. The tissue graft material 45 may be incorporated, for example, in the form of (a) strip(s) wrapped around the stem 34, 34', 34", 34''', 34'''', (a) disk(s) with (a) central opening(s) threaded onto the stem 34, 34', 34", 34''', 34'''', or tissue graft material otherwise inserted into the fistula 20 prior to or during sealing of the fistula 20 with the device 22, 22', 22", 22''', 22''''.

In another embodiment illustrated in FIG. 8, the body 40 of a voice prosthesis device 42 is used to maintain a tracheoesophageal fistula 43 patent, for example for the reasons illustrated and described in any of U.S. Pat. Nos. 4,435,853; 4,596,579; 4,614,516; 4,820,304; 4,911,716; 5,064,433; 5,300,119; 5,507,809; 5,571,180; 5,919,231; 6,776,797; RE39,923; and, 7,520,897 to permit alaryngeal speech. Again, the disclosures of these references are hereby incorporated herein by reference. This listing is not intended as a representation that a complete search of all relevant prior art has been conducted, or that no better references than those listed exist. Nor should any such representation be inferred. Body 40 is a hollow tube constructed of an elastomeric material, again, such as a suitable silicone. With reference to FIG. 8a, the elastomeric character of body 40 or stem 34, 34', 34", 34''', 34'''' can be provided or enhanced by incorporation into the stem 34, 34', 34", 34''', 34'''' or body 40 of a spring 47 constructed of a suitable material, for example, a steel or plastic helical coil spring, the axis of which extends parallel with the stem 34, 34', 34", 34''', 34'''' or body 40 axis or forms at least a portion of the length of the stem 34, 34', 34", 34''', 34''''.

Along its length, typically remote from its internal valve(s) (not shown) to reduce interference with the operation of that (those) valve(s), the sidewall of body 40 includes a corrugated section 44. Device 42 is provided adjacent its ends 46, 48 with flanges 50, 51 for orienting in a continuously sealing manner against the anterior wall 52 of the esophagus and the posterior wall 55 of the trachea, respectively, in use. These devices 42 are fitted to the wearer 54. Generally, a length between flanges 50, 51 is chosen that will not quite span the tracheoesophageal tissue 56 of the wearer 54. Thus, the device 42 is partially, but not fully, extended from its unstressed, manufactured length. Thus, as the tracheoesophageal tissue 56 thickens or thins, owing to various phenomena, the section 44 accommodates the attendant increase or decrease in the length body 40 must span. When the tracheoesophageal tissue 56 returns to its prior condition, device 42 returns to its prior length.

In the fitting of devices 22, 22', 22", 22''', 22'''', 42 of the types illustrated and described herein, the clinician may fit a device 22, 22', 22", 22''', 22'''', 42 which is in the middle of the range of fluctuation of the thicknesses of the tissue through which the fistula extends. For example, for a tissue thickness which may fluctuate between 3 and 9 millimeters, a device with a 6 millimeter length between its flanges may be fitted; for a tissue thickness which may fluctuate between 9 millimeters and 15 millimeters, a device with a 12 millimeter length between its flanges may be fitted, and so on. In different applications, the range of fluctuation may be different from 6 millimeters and the optimal length for the device may lie somewhere other than in the middle of that range, but this establishes the principle that the elastomeric shaft 34, 34', 34", 34''', 34'''', 40 maintains the fluid-tight seal between the flanges 24, 28; 24', 28; 24", 28"; 24''', 28'''; 24'''', 28''''; and, 50, 51 and their respective walls 26, 30; 26''', 30'''; 26'''', 30''''; and, 52, 55 of the tissue throughout the anticipated range. While only a single stem 34, 34', 34", 34''', 34'''', 40 is illustrated in each of these embodiments, a device 22, 22', 22", 22''', 22'''', 42 may be constructed including multiple stems providing similar behavior of the flanges as the tissue through which the fistula extends swells and recedes.

Two graphs of applied force between the ends 46, 48 of such a device 42 and resulting change in length between the ends 46, 48 of the device 42 illustrate a principle of these embodiments. As these Figures illustrate, the device 42, including a tubular body 40 having a corrugated wall section 44, exhibits an elongation between the ends 46, 48, in the range of elongation of about 0 mm to about 15 mm or so, of greater than about 0.6 mm/N of force applied between the first and second flanges 50, 51. A straight line with that slope fits this region of the 8 mm, 17F Provox® curve fairly closely. In that range of elongation (about 0 mm to about 15 mm or so), the 8 mm, 17F Provox® device's curve is the closest one to the curve of the device 42's performance, labeled "FIG. 8 7 mm 0.3 mm CORRUGATED." The curve of the device 42's performance has a slope in the range of about 1.4 mm/N in the range of elongation of about 0 mm to about 15 mm or so. The devices, testing of which generated these graphs, were a number of prior art voice prosthesis devices from different manufacturers and voice prosthesis devices 42 constructed as illustrated in FIGS. 5, 6 and 8. The sources, lengths, outside diameters and wall thicknesses of the prior art devices and the devices 42 constructed as illustrated in FIGS. 5, 6 and 8, are listed in the following Table I.

TABLE I

Comparison of Prior Art Devices to Device Constructed According to Description

Figure 9:
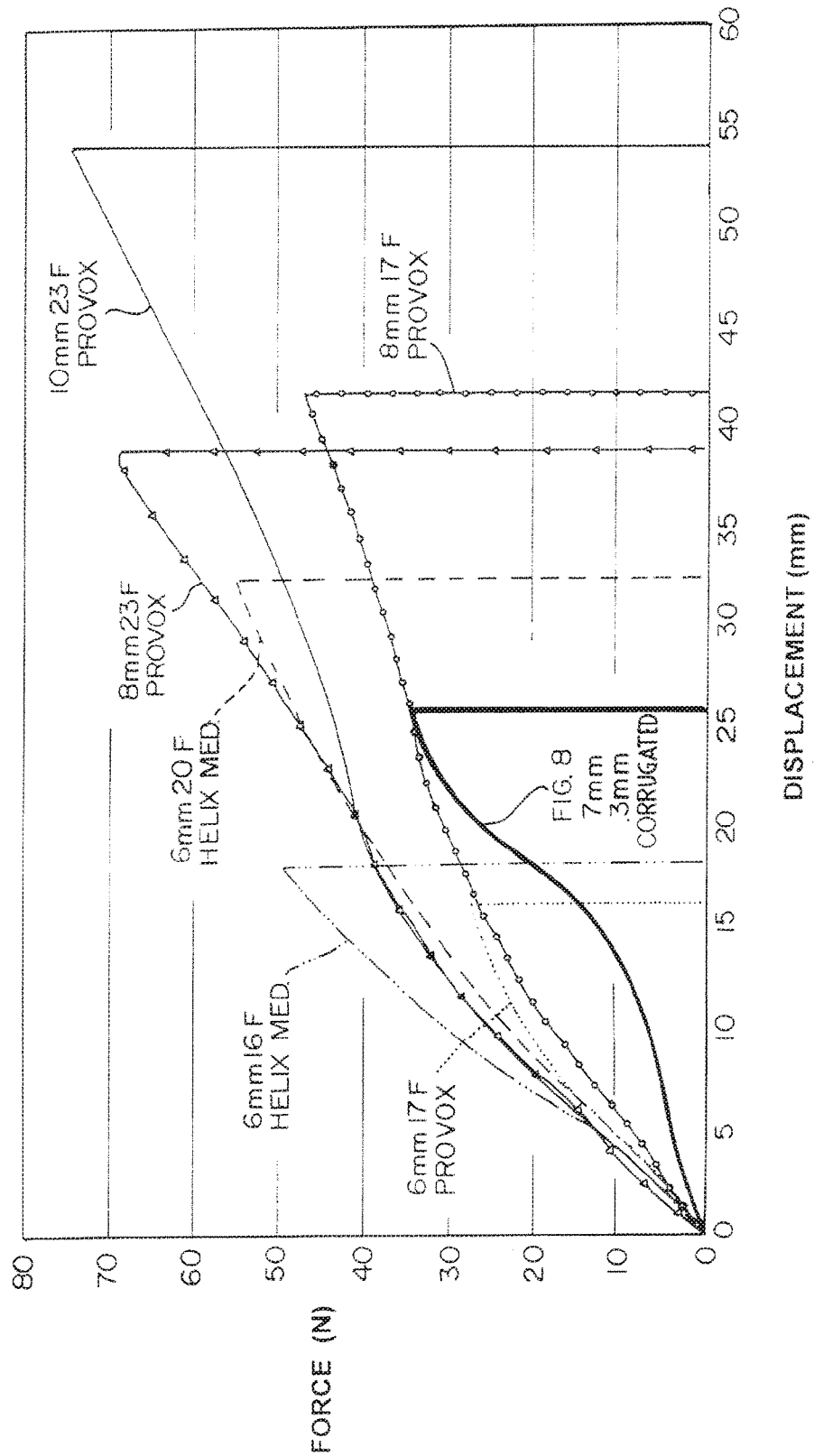
FIG. 9 illustrates graphs of elongation (displacement in the drawing) versus applied force between the ends of several prior art devices and a device constructed according to the disclosure.

| Source | Length | Size (Outside Diameter) | Symbol, FIGS. 9-10 |
| --- | --- | --- | --- |
| InHealth (average over five devices | 6 mm | 16 French | —··—·· |
| InHealth (average over five devices) | 6 mm | 20 F | - - - - - |
| Atos ® Provox ® | 6 mm | 17 F | ············ |
| Atos ® Provox ® | 8 mm | 17 F | —o—o— |
| Atos ® Provox ® | 8 mm | 23 F | —△—△— |
| Atos ® Provox ® | 10 mm | 23 F | ——— |
| FIG. 8 | 7 mm | 20 F, .3 mm corrugated | ——— |

The second of these graphs, FIG. 10, is an enlarged version of the portion of FIG. 9 between zero elongation and about 15 mm elongation. The device 42 is constructed from 60 durometer silicone, has an about 0.3 mm (about 0.012 inch) sidewall thickness in the corrugation region 44 and is provided with two and a half corrugations of semicircular (wave-like) cross-section as illustrated in FIGS. 5-6, in its sidewall. As FIGS. 9-10 illustrate, throughout the region of applied force of interest, the elongation per unit applied force of the device 42 is appreciably greater than those of the tested prior art devices. Additionally, the device 42 readily returns to its unstressed configuration (compare FIGS. 6 and 5) when the elongating force is removed, making the configuration ideal for use in a device 42 for maintaining a fistula 43 sealed. As the tracheoesophageal tissue 56 swells and shrinks, the tubular body 40 readily elongates and contracts lengthwise (again, compare FIGS. 5 and 6) along its axis between its tracheal flange 51 and its esophageal flange 50, keeping both flanges 50, 51 continuously sealed against their respective walls 52, 55.

In another set of tests, prior art Helix Medical®/InHealth Technologies® 6 mm long, 20 F, 0.46 mm (.about.0.018 in.) wall thickness, Helix/InHealth 4 mm long, 16 F, 0.46 mm (.about.0.018 in.) wall thickness and long Atos® Provox® NID 10 mm long, 23 F, 0.58 mm (.about.0.023 in.) wall thickness devices were tested against devices 42 of 7 mm length, 20 F, 0.46 mm (.about.0.018 in.) sidewall thickness in the corrugation region, 7 mm length, 20 F, 0.3 mm (.about.0.012 in.) inch sidewall thickness in the corrugation region and 6 mm length, 20 F, 0.36 mm (.about.0.014 in.) inch sidewall thickness in the corrugation region. All devices were constructed from 60 Durometer silicone except as noted. These tests are summarized in the following Table II.

TABLE II

Comparison of Prior Art Devices
to Device Constructed According to Description

| Size | Wall Thickness | Durometer | Operating Range |
|---|---|---|---|
| InHealth 20 F, 6 mm length (average over five devices) | .46 mm (~.018 in.) | 60 | 1 mm elongation |
| InHealth 16 F, 4 mm length (average over five devices) | .46 mm (~.018 in.) | 60 | 2 mm elongation |
| Atos ® Provox ® NID, 23 F 10 mm length | .58 mm (~.023 in.) | unknown | <1 mm elongation |
| Device 42 20 F, 7 mm | .46 mm (~.018 in.) | 60 | >6 mm elongation |
| Device 42 20 F, 7 mm | .3 mm (~.012 in.) | 60 | >6 mm elongation |
| Device 42 20 F, 6 mm | .36 mm (~.014 in.) | 60 | >7 mm elongation |

As can be seen from Table II, the devices 42 constructed as described all continued to operate satisfactorily at elongations greater than 6 mm. The prior art devices, all of generally similar configuration but, of course, without the corrugated region failed at elongations less than a third of that (<1 to 2 mm elongation). All devices then continued to be stretched until they failed destructively. All of the prior art devices failed by tearing at the valve seat, and all of the devices 42 failed by tearing at about the middle of the corrugated region. As noted in the table, much less force is needed to elongate the 7 mm long, 20 F, 0.46 mm (.about.0.018 in.) wall thickness devices 42, the 7 mm long, 20 F, 0.3 mm (.about.0.012 in.) wall thickness devices 42, and the 6 mm long, 20 F, 0.36 mm (.about.0.014 in.) wall thickness devices 42 than the prior art devices tested. The devices 42 also exhibited much less distortion of their internal valves during testing. The prior art devices' valves became twisted and distorted inside the device body after <1 mm of axial elongation. In a voice prosthesis device, twisting or distortion of the valve is, of course, considered a failure.

Although the 10 mm 23 F Atos® Provox® NID device provided the most axial elongation, it required about four times as much force to provide approximately 10 mm of elongation as did the 7 mm, 20 F, 0.3 mm (.about.0.012 in.) wall thickness device 42. The forces needed to elongate the devices 42 to this range of elongation are believed to be well above the forces exhibited on such devices by swelling tissue 56 in the wearer 54. Consequently, it is believed that the devices 42 will perform through multiple cycles of such elongation and retraction occasioned by swelling and shrinking of the tissue 56.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An adjustable device for sealing a fistula including a first flange for orienting against a first wall of the fistula, a second flange for orienting against a second wall of the fistula, and at least one stem coupling the first and second flanges, the at least one stem passing through a respective at least one opening provided in at least one of the first and second flanges to permit adjustment of the location of said at least one of the first and second flanges along a length of the at least one stem, the at least one stem exhibiting an elongation of greater than about 0.65 mm/N of force applied between the first and second flanges in a range of elongation between 0 mm to about 15 mm.

2. The device of claim 1, wherein one of the first and second flanges and the stem are formed integrally.

3. The device of claim 1, wherein at least one of the first and second flanges comprises an elastomeric flange.

4. The device of claim 1, wherein the stem is provided with enlargements at intervals along its length.

5. The device of claim 4, wherein the enlargements comprise somewhat spherical-, disk-, cone- or arrowhead-shaped enlargements.

6. The device of claim 4, wherein the enlargements are substantially uniformly spaced along at least a portion of the length of the stem.

7. The device of claim 1, wherein the first and second flanges are generally circular in plan view.

8. An adjustable device for sealing a fistula including a first flange for orienting against a first wall of the fistula, a second flange for orienting against a second wall of the fistula, and at least one stem coupling the first and second flanges, the at least one stem having first and second ends being fixedly attached with the first and second flanges, the at least one stem exhibiting an elongation of greater than about 0.65 mm/N of force applied between the first and second flanges in a range of elongation between 0 mm to about 15 mm.

9. The device of claim 8, wherein at least one of the first and second flanges and the stem are formed integrally.

10. The device of claim 8, wherein the first and second flanges and the stem are formed integrally.

11. The device of claim 8, wherein at least one of the first and second flanges comprises an elastomeric flange.

12. The device of claim 8, wherein the first and second flanges are generally circular in plan view.

13. An adjustable device for sealing a fistula including a first flange for orienting against a first wall of the fistula, a second flange for orienting against a second wall of the fistula, and at least one stem coupling the first and second flanges, the at least one stem defining a hollow tubular wall extending between the first flange and the second flange, the at least one stem exhibiting an elongation of greater than about 0.65 mm/N of force applied between the first and second flanges in a range of elongation between 0 mm to about 15 mm.

14. The device of claim 13, wherein at least one of the first and second flanges and the stem are formed integrally.

15. The device of claim 13, wherein the first and second flanges and the stem are formed integrally.

16. The device of claim 13, wherein at least one of the first and second flanges comprises an elastomeric flange.

17. The device of claim 13, wherein the first and second flanges are generally circular in plan view.

18. The device of claim 13, wherein the hollow tubular wall includes a corrugated section.

19. The device of claim 13, wherein the hollow tubular wall includes a spring therein.

* * * * *